(12) United States Patent
Ono et al.

(10) Patent No.: US 10,072,113 B2
(45) Date of Patent: Sep. 11, 2018

(54) COMPOSITION, CURABLE COMPOSITION, PRODUCTION METHOD THEREFOR, AND CURED PRODUCT

(71) Applicant: SHOWA DENKO K.K., Tokyo (JP)

(72) Inventors: Katsutoshi Ono, Tokyo (JP); Tomomitsu Kato, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 204 days.

(21) Appl. No.: 14/906,791

(22) PCT Filed: Jul. 22, 2014

(86) PCT No.: PCT/JP2014/069308
§ 371 (c)(1),
(2) Date: Jan. 21, 2016

(87) PCT Pub. No.: WO2015/012258
PCT Pub. Date: Jan. 29, 2015

(65) Prior Publication Data
US 2016/0168295 A1    Jun. 16, 2016

(30) Foreign Application Priority Data
Jul. 25, 2013 (JP) ................................ 2013-154947

(51) Int. Cl.
| | | |
|---|---|---|
| C08F 220/36 | (2006.01) | |
| C07C 265/04 | (2006.01) | |
| C07C 271/04 | (2006.01) | |
| C08F 20/34 | (2006.01) | |

(52) U.S. Cl.
CPC .......... C08F 220/36 (2013.01); C07C 265/04 (2013.01); C07C 271/04 (2013.01); C08F 20/34 (2013.01)

(58) Field of Classification Search
CPC ..... C07C 265/04; C07C 271/04; C08F 20/34; C08F 220/36
USPC ....................................................... 526/312
See application file for complete search history.

(56) References Cited

U.S. PATENT DOCUMENTS

| | | | |
|---|---|---|---|
| 2,821,544 A | 1/1958 | Holtschmidt | |
| 4,310,688 A | 1/1982 | Mendoza | |
| 6,245,935 B1 | 6/2001 | Misu et al. | |
| 2002/0013492 A1 | 1/2002 | Nishioka et al. | |
| 2011/0281025 A1 | 11/2011 | Arai et al. | |

FOREIGN PATENT DOCUMENTS

| | | | | |
|---|---|---|---|---|
| CN | 102007119 A | | 4/2011 | |
| CN | 102301449 A | | 12/2011 | |
| EP | 0 477 376 A1 | | 4/1992 | |
| EP | 0 976 723 A2 | | 2/2000 | |
| EP | 2377847 | * | 10/2011 | ........... C07C 263/08 |
| JP | 03-275661 A | | 12/1991 | |
| JP | 05-262715 A | | 10/1993 | |
| JP | 09-059244 A | | 3/1997 | |
| JP | 11-043527 A | | 2/1999 | |
| JP | 2000-044529 A | | 2/2000 | |
| KR | 1020060054381 A | | 5/2006 | |
| KR | 1020100009602 A | | 1/2010 | |
| TW | 200911853 A | | 3/2009 | |
| TW | 201136959 A | | 11/2011 | |
| TW | 201207556 A | | 2/2012 | |

OTHER PUBLICATIONS

Communication dated Aug. 2, 2017, from the Taiwan Intellectual Property Office in counterpart application No. 103125112.
Communication dated Aug. 2, 2016 from the State Intellectual Property Office of the P.R.C. in counterpart application No. 201480040270.3.
"Coating Process: Training class of Coating Technology from Ministry of Fuel Chemistry Industry," Petroleum Chemical Industry Press; vol. 5, Apr. 1976 (7 pages total, including p. 101).
Communication dated Dec. 1, 2016, issued by the Korean Intellectual Property Office in corresponding Korean Application No. 10-2016-7000731.
Tadashi Hashimoto et al., "Nippon Gomu Kyokaishi," The Journal of our Society, 1972, pp. 452-461, vol. 45, No. 5.
International Search Report of PCT/JP2014/069308 dated Oct. 28, 2014.

* cited by examiner

Primary Examiner — Wenwen Cai
(74) Attorney, Agent, or Firm — Sughrue Mion, PLLC

(57) ABSTRACT

A composition is provided which includes a polymerizable compound (A) which includes a (meth)acryloyl group and an isocyanate group in a molecule thereof; and a reaction accelerator (B) which is a compound including a (meth)acryloyl group and a halogenated carbamoyl group in a molecule.

7 Claims, 4 Drawing Sheets

COMPOSITION, CURABLE COMPOSITION, PRODUCTION METHOD THEREFOR, AND CURED PRODUCT

CROSS REFERENCE TO RELATED APPLICATIONS

This is a National Stage of International Application No. PCT/JP 2014/069308filed Jul. 22, 2014 (claiming priority based on Japanese Patent Application No. 2013-154947 filed Jul. 25, 2013), the contents of which are incorporated herein by reference in their entirety.

TECHNICAL FIELD

The present invention relates to a composition including a polymerizable compound and a reaction accelerator, a curable composition obtained using the composition and a production method therefor, and a cured product formed by curing the curable composition.

Priority is claimed on Japanese Patent Application No. 2013-154947, filed on Jul. 25, 2013, the contents of which are incorporated herein by reference.

BACKGROUND OF THE INVENTION

Since a polymerizable compound including a (meth) acryloyl group and an isocyanate group in a molecule has two kinds of reaction points having different reactivities, a reaction can be carried out in two stages. For example, a (meth)acryloyl group of a reaction product can be reacted (radical polymerization or the like with the same polymerizable compound or another polymerizable compound) with another compound after a reaction (urethanization reaction or the like with a compound having a hydroxyl group) of an isocyanate group of the polymerizable compound with another compound. On the contrary, an isocyanate group of a reaction product can be reacted with another compound after a reaction of a (meth)acryloyl group of the polymerizable compound with another compound. For this reason, the above-described polymerizable compound is used, as a raw material, for a wide range of applications such as coating materials, inks, adhesives, coating agents, or molding resins.

When the above-described polymerizable compound is reacted with another compound, a catalyst is used to accelerate the reaction. For example, as a catalyst which is used to react the above-described polymerizable compound with a hydroxyl group of another compound to obtain a urethane compound, an amine-based catalyst or a metal catalyst such as dibutyl tin dilaurate is normally used (Non Patent document 1).

However, these catalysts have problems in that some substrates do not show reaction accelerating effects sufficiently. When a catalyst remains in a reaction product, this occasionally adversely affects the physical properties of the reaction product, the physical products of a cured product thereof, or the like.

Therefore, in addition to using these catalysts, a technique of accelerating the reaction of a polymerizable compound including a (meth)acryloyl group and an isocyanate group in a molecule has been required.

BACKGROUND ART DOCUMENTS

Non Patent Documents

Non Patent document 1: Nippon Gomu Kyokaishi, the Journal of our Society. 1972, Vol. 45, No. 5, p. 452 to 461

DISCLOSURE OF INVENTION

Problem to be Solved by the Invention

The present invention has been made in consideration of the above-described problem and an object thereof is to provide a composition in which the reactivity of a polymerizable compound including a (meth)acryloyl group and an isocyanate group in a molecule is improved, a curable composition obtained using the composition, a production method therefor, and a cured product.

Means for Solving the Problem

As a result of intensive research conducted to solve the above-described problem, the present inventors found that a compound including a (meth)acryloyl group and a halogenated carbamoyl group in a molecule has an effect of improving the reactivity (reactivity of an isocyanate group and reactivity of a (meth)acryloyl group) of a polymerizable compound including a (meth)acryloyl group and an isocyanate group in a molecule.

For example, a polymerizable compound shows excellent reactivity during the reaction (urethanization reaction or the like) of the polymerizable compound with another compound having active hydrogen when the above-described compound exists in a reaction system as a reaction accelerator. Further, the polymerizable compound or a reaction product generated due to a reaction of the polymerizable compound with another compound having active hydrogen shows excellent reactivity during a radical polymerization reaction and curing properties of a curable composition containing the polymerizable compound or the reaction product are improved.

The present invention is based on the above-described knowledge and has the following aspects.

[1] A composition including: a polymerizable compound (A) which includes a (meth)acryloyl group and an isocyanate group in a molecule thereof; and a reaction accelerator (B) which is a compound including a (meth)acryloyl group and a halogenated carbamoyl group in a molecule thereof.

[2] The composition according to [1], in which the amount of the reaction accelerator (B) is in a range of 5 ppm by mass to 20000 ppm by mass with respect to the amount of the polymerizable compound (A).

[3] The composition according to [1] or [2], in which the amount of the reaction accelerator (B) is in a range of 5 ppm by mass to 8000 ppm by mass with respect to the amount of the polymerizable compound (A).

[4] The compound according to any one of [I] to [3], in which the polymerizable compound (A) is a compound represented by the following general formula (1) or (1').

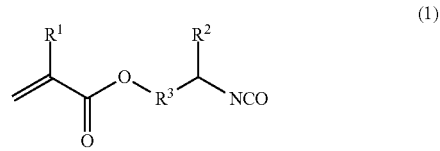

(1)

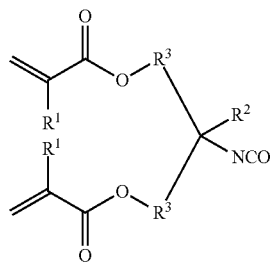

(1')

[In the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond, and a phenylene bond, and two $R^1$'s in the formula (1') may be the same as or different from each other and two $R^3$'s may be the same as or different from each other.]

[5] The composition according to any one of [1] to [4], in which the reaction accelerator (B) is a compound represented by the following general formula (2) or (2').

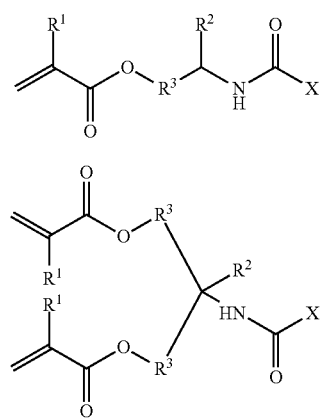

[In the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond, and a phenylene bond, X represents a fluorine atom, a chlorine atom, a bromine atom, or an iodine atom, and two $R^1$'s in the formula (2') may be the same as or different from each other and two $R^3$'s may be the same as or different from each other.]

[6] The composition according to [5], in which the polymerizable compound (A) contains a compound represented by the formula (1) or (1'), and the reaction accelerator (B) contains a compound which is represented by the formula (2) or (2') and in which $R^1$, $R^2$, and $R^3$ in the formula (2) or (2') respectively have the same definitions as those for $R^1$, $R^2$, and $R^3$ of the polymerizable compound (A).

[7] The composition according to any one of [1] to [6], further including a compound which includes an active hydrogen-containing group.

[8] The composition according to [7], in which the active hydrogen-containing group is at least one selected from a group consisting of a hydroxyl group, a mercapto group, a carboxyl group, and an amino group.

[9] A curable composition which is formed by reacting the polymerizable compound (A) with the compound including the active hydrogen-containing group in the composition according to [8] and which includes a polymerizable compound which comprises a (meth)acryloyl group and at least one selected from a group consisting of a urethane bond, a thiourethane bond, an amide bond and a urea bond in a molecule.

[10] A method of producing a curable composition including: a step of reacting the polymerizable compound (A) with the compound including the active hydrogen-containing group in the composition according to [8] to obtain a curable composition which includes a polymerizable compound wherein the compound comprises a (meth)acryloyl group and at least one selected from a group consisting of a urethane bond, a thiourethane bond, an amide bond and a urea bond in a molecule.

[11] A cured product which is formed by curing the curable composition according to [9].

Effects of the Invention

According to the present invention, it is possible to provide a composition in which the reactivity of a polymerizable compound including a (meth)acryloyl group and an isocyanate group in a molecule is improved, a curable composition obtained using the composition, a production method therefor, and a cured product.

Figure 1:
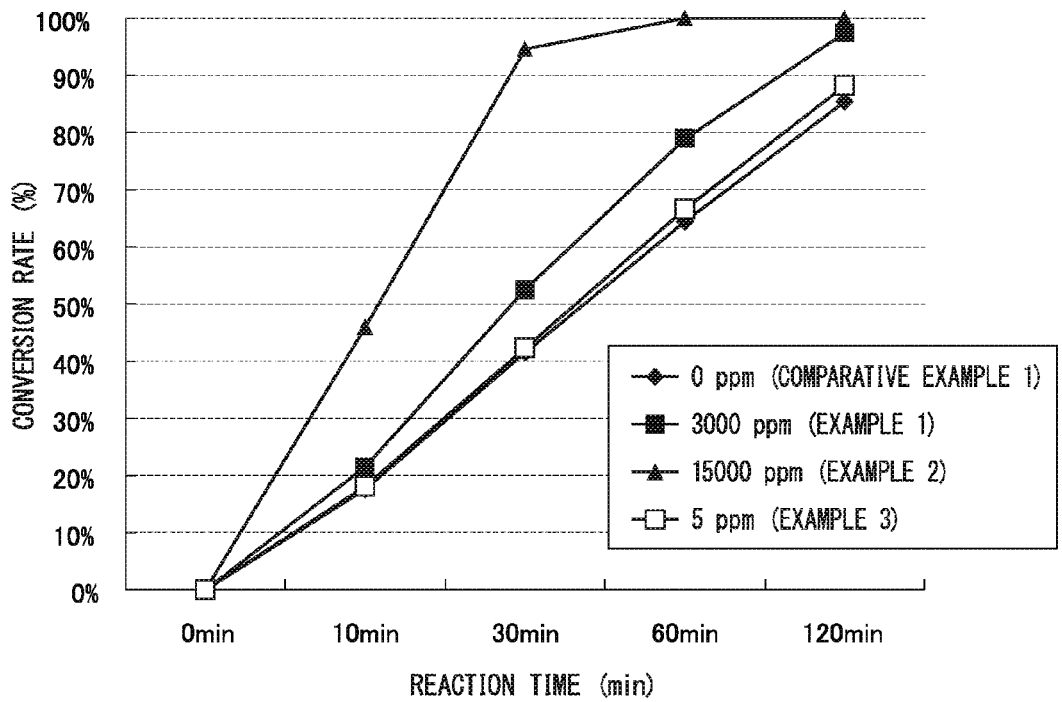
FIG. 1 is a graph showing results of Examples 1 to 3 and Comparative Example 1 in which a urethanization reaction of MOI is performed (change in the conversion ratio of an isocyanate group of MOI to urethane with time (urethanization rate)).

BEST MODE FOR CARRYING OUT THE INVENTION (Composition)

A composition (hereinafter, also referred to as a composition (I)) of a first aspect of the present invention includes a polymerizable compound (A) having a (meth)acryloyl group and an isocyanate group in a molecule and a reaction accelerator (B) which is a compound having a (meth)acryloyl group and a halogenated carbamoyl group in a molecule.

In the present invention, a "(meth)acryloyl group" indicates an acryloyl group ($CH_2$=CH—CO—) or a methacryloyl group ($CH_2$=C($CH_3$)—CO—).

A "halogenated carbamoyl group" indicates a group having a structure represented by >N—CO—Z (Z represents a halogen atom). Examples of the halogen atom include a fluorine atom, a chlorine atom, a bromine atom, and an iodine atom.

In the composition (I), the reaction accelerator (B) plays a role of improving reactivity of the polymerizable compound (A). The polymerizable compound (A) includes a (meth)acryloyl group and an isocyanate group as a reactive functional group and the reaction accelerator (B) can improve both of the reactivity of the (meth)acryloyl group and the reactivity of the isocyanate group. For example, in regard to the (meth)acryloyl group, the reaction rate at the time when radical polymerization of the polymerizable compound (A) is carried out in the composition (I) increases. Further, in regard to the isocyanate group, the reaction rate between the isocyanate group and an active hydrogen-containing group increases in a case where the composition (I) includes a compound having an active hydrogen-containing group such as a hydroxyl group.

The reaction accelerator (B) particularly exhibits an excellent effect of improving the reactivity of the isocyanate group of the polymerizable compound (A) (improvement of the reaction rate between the isocyanate group and the active hydrogen-containing group).

(Polymerizable Compound (A))

The polymerizable compound (A) is a compound having a (meth)acryloyl group and an isocyanate group in a molecule.

A compound represented by the following general formula (1) or (1') is preferable as the polymerizable compound (A) in terms of ease of obtaining raw materials and reactivity.

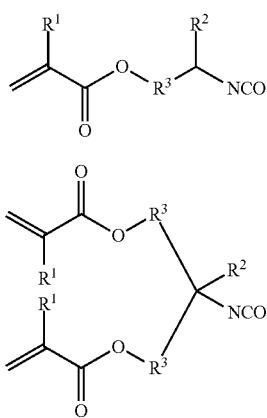

[In the formula, $R^1$ and $R^2$ each independently represent a hydrogen atom or a methyl group and $R^3$ represents an alkylene group which may include a substituent and has 1 to 10 carbon atoms or a group formed by substituting a single bond between carbon atoms of the alkylene group with a bond selected from a group consisting of an ether bond, an ester bond, and a phenylene bond. Two $R^1$'s in the formula (1') may be the same as or different from each other and two $R^3$'s may be the same as or different from each other.]

The alkylene group in the present invention means a group generated by removing two arbitrary hydrogen atoms bonded to a carbon atom in aliphatic saturated hydrocarbon.

As the alkylene group having 1 to 10 carbon atoms, in $R^3$, in the formula (1) or (1'), an alkylene group having 1 to 8 carbon atoms is preferable, an alkylene group having 1 to 6 carbon atoms is more preferable, and an alkylene group having 1 to 4 carbon atoms is still more preferable.

As the alkylene group in $R^3$, a linear or branched chain alkylene group is preferable and a linear alkylene group is more preferable.

In the alkylene group, a single bond between carbon atoms in the alkylene group may be substituted with a bond selected from a group consisting of an ether bond (—O—), an ester bond (—CO—O—), and a phenylene bond (—$C_6H_4$—). The number of the single bond to be substituted with the bond may be one or two or greater, but is preferably one. In a case where two or more single bonds are substituted, bonds to be substituted with the respective single bonds may be the same as or different from each other.

Preferred specific examples of the alkylene group or the group which is formed by substituting a single bond between carbon atoms of the alkylene group with a bond selected from a group consisting of an ether bond, an ester bond, and a phenylene bond include —$CH_2$—, —$C_2H_4$—, —($CH_2$)$_3$—, —($CH_2$)$_4$—, —($CH_2$)—, —($CH_2$)$_6$—, —$CH_2$—O—$C_2H_4$—, —$C_2H_4$—COO—$CH_2$—, and —$C_2H_4$-Ph-$CH_2$—.

In $R^3$, the alkylene group or the group which is formed by substituting a single bond existing between carbon atoms of the alkylene group with a bond selected from a group consisting of an ether bond, an ester bond, and a phenylene bond may include a substituent.

Examples of the substituent include a hydrocarbon group, a nitro group, a cyano group, —OR', —COR', and —COOR' (R' represents an alkyl group).

In a case where $R^3$ includes a phenylene bond, a hydrogen atom in the alkylene group may be substituted with the substituent, or hydrogen atom of the phenylene bond may substitute with the substituent.

The hydrocarbon group as the substituent is not particularly limited and examples thereof include a hydrocarbon group having 1 to 10 carbon atoms. Preferable examples thereof include a hydrocarbon having 1 to 6 carbon atoms and more preferable examples thereof include a methyl group, an ethyl group, a propyl group, an isopropyl group, a butyl group, an isobutyl group, a t-butyl group, a cyclopentyl group, a vinyl group, a cyclohexyl group, and a phenyl group.

As an alkyl group which is R', an alkyl group having 1 to 10 carbon atoms is exemplified. Preferable examples thereof include an alkyl group having 1 to 6 carbon atoms and more preferable examples thereof include a methyl group, an ethyl group, a propyl group, an isopropyl group, a butyl group, an isobutyl group, a t-butyl group, and a cyclopentyl group.

As $R^3$, among the above examples, an alkylene group having 1 to 8 carbon atoms or a group formed by substituting at least one single bond between carbon atoms of said alkylene group with an ether bond is preferable. An alkylene group having 1 to 6 carbon atoms or a group formed by substituting at least one single bond between carbon atoms of said alkylene group with an ether bond is more preferable. An alkylene group having 1 to 4 carbon atoms or a group formed by substituting at least one single bond between carbon atoms of said alkylene group with an ether bond is still more preferable, and —CH$_2$—, —C$_2$H$_4$—, —(CH$_2$)$_3$—, —CH$_2$—O—C$_2$H$_4$—, or —C$_2$H—O—C$_2$H$_4$— is particularly preferable.

Specific examples of the compound represented by the formula (1) include (meth)acryloyloxy methyl isocyanate, (meth)acryloyloxy ethyl isocyanate, (meth)acryloyloxy propyl isocyanate, (meth)acryloyloxy butyl isocyanate, (meth)acryloyloxy pentyl isocyanate, (meth)acryloyloxy hexyl isocyanate, (meth)acryloyloxy heptyl isocyanate, (meth)acryloyloxy octyl isocyanate, (meth)acryloyloxy nonyl isocyanate, (meth)acryloyloxy decyl isocyanate, and (meth)acryloyloxy ethoxy ethyl isocyanate. Among these, in terms of obtaining raw materials and reactivity, (meth)acryloyloxy ethyl isocyanate or (meth)acryloyloxy ethoxy ethyl isocyanate is preferable.

Specific preferable examples of the compound represented by the formula (1') include 1,1-(bisacryloyloxymethyl)ethyl isocyanate.

(Reaction Accelerator (B))

The reaction accelerator (B) is a compound including a (meth)acryloyl group and a halogenated carbamoyl group in a molecule.

In terms of ease of obtaining raw materials and reactivity, a compound represented by the following general formula (2) or (2') is preferable as the reaction accelerator (B).

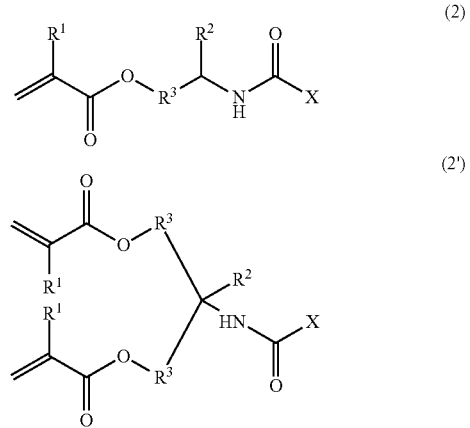

[In the formula, R$^1$ and R$^2$ each independently represent a hydrogen atom or a methyl group, R$^3$ represents an alkylene group which may include a substituent and has 1 to 10 carbon atoms or a group formed by substituting a single bond between carbon atoms of the alkylene group with a bond selected from a group consisting of an ether bond, an ester bond, and a phenylene bond, and X represents a fluorine atom, a chlorine atom, a bromine atom, or an iodine atom. Two R$^1$'s in the formula (2') may be the same as or different from each other and two R$^3$'s may be the same as or different from each other.]

Structures and preferable ranges of R$^1$, R$^2$, and R$^3$ in the formula (2) or (2') are the same as the structures and preferable ranges of R$^1$, R$^2$, and R$^3$ in the formula (1) or (1').

X may represent any one of a fluorine atom, a chlorine atom, a bromine atom, and an iodine atom, and a chlorine atom is preferable.

As specific examples of the compound represented by the formula (2), a compound obtained by substituting an isocyanate group (—NCO) of the compound exemplified as a specific example of the compound represented by the formula (1) with —NH—CO—X can be cited, and N-(meth)acryloyloxy ethyl carbamoyl chloride or N-(meth)acryloyloxy ethoxy ethyl carbamoyl chloride is preferably used.

As specific examples of the compound represented by the formula (2'), a compound obtained by substituting an isocyanate group (—NCO) of the compound exemplified as a specific example of the compound represented by the formula (2') with —NH—CO—X can be cited, and N-1,1-(bisacryloyloxymethyl)ethyl carbamoyl chloride is preferably used.

(Quantity Ratio of Reaction Accelerator (B) to Polymerizable Compound (A))

The amount of the reaction accelerator (B) in the composition (I) is preferably in a range of 5 ppm by mass to 20000 ppm by mass, more preferably in a range of 5 ppm by mass to 8000 ppm by mass, and is still more preferably in a range of 5 ppm by mass to 3000 ppm by mass with respect to the amount of the polymerizable compound (A) (100% by mass).

In a case where the content ratio of the reaction accelerator (B) to the polymerizable compound (A) is less than 5 ppm by mass, the reaction acceleration effects may not be sufficiently obtained.

In a case where the content ratio of the reaction accelerator (B) to the polymerizable compound (A) exceeds 20000 ppm by mass, reactions of an isocyanate group and a (meth)acryloyl group in the polymerizable compound (A) are both accelerated and inconvenience may occur. As a method of using a compound having two different kinds of reactive functional groups such as the polymerizable compound (A), a method is frequently used wherein a reaction is performed at two stages, that is, one of the two different groups (for example, the isocyanate group) of the compound is reacted with another compound, and then the other group of the two different groups (for example, the (meth)acryloyl group) is subsequently reacted. However, when a large amount of the reaction accelerator (B) exists, the second stage reaction may occur during the first stage reaction or during storage of the composition before the first stage reaction is performed so that an unwanted reaction product may be generated. Accordingly, depending on the method of using the polymerizable compound (A), it is preferable that the amount of the reaction accelerator (B) to be added be set to 20000 ppm by mass or less and particularly 8000 ppm by mass or less with respect to the amount of the polymerizable compound (A).

(Method of Measuring Amount of Reaction Accelerator (B) in Composition (I))

For example, the following two kinds of measurement methods 1 and 2 are exemplified as a method of acquiring the amount of the reaction accelerator (B) contained in the composition (I). Further, the following measurement conditions (the amount of samples to be used, the kind of reagent, an NMR machine, the number of times NMR is integrated, and the like) are merely examples and the conditions may be appropriately changed if necessary (particularly in a case where the amount of the reaction accelerator (B) to be contained is small, the conditions of the measurement method 2 may need to be changed into those with high precision).

(Measurement Method 1: Silver Nitrate Titration Method (Reference: JIS K1603-3))

A 100 mL methanol aqueous solution (water:methanol=3:7) and 10 g of a sample to be measured are added to a 200 mL capacity beaker and the mixture is stirred and dissolved. The solution is titrated by a silver nitrate aqueous solution (0.02 mol/L, titer 1.006, manufactured by Kanto Kagaku), the equivalent point is measured, and the amount of the reaction accelerator (B) in the sample is acquired using the following formula.

Amount (%) of reaction accelerator (B)=(titration value (L) of silver nitrate aqueous solution×titer 1.006×molecular weight of chloride 35.46 (g/mol)×molar concentration of silver nitrate aqueous solution 0.02 (mol/L)×100)/amount of samples (g)

(Measurement Method 2: NMR Measurement)
(Conditions)

100 mg of a sample to be measured is dissolved in 0.3 mL of dehydrated benzene d6 in a 5 mmΦ NMR sample tube to prepare a sample for measurement and a $^1$H-NMR spectrum of the sample for measurement is measured under the following conditions.

Device: Avance-400, manufactured by Bruker BioSpin Corporation

Measurement temperature: room temperature

Pulse width: 30°

Pulse repetition time: 5 seconds

Number of times of integration: 128 times (Quantitative Method)

Hereinafter, a method of acquiring the amount of the reaction accelerator (B) from NMR using samples to be measured in which the polymerizable compound (A) is methacryloyloxy ethyl isocyanate (hereinafter, referred to as MOI) and the reaction accelerator (B) is methacryloyloxy ethyl carbamoyl chloride (hereinafter, referred to as MOC) is shown below as an example.

Figure 5:
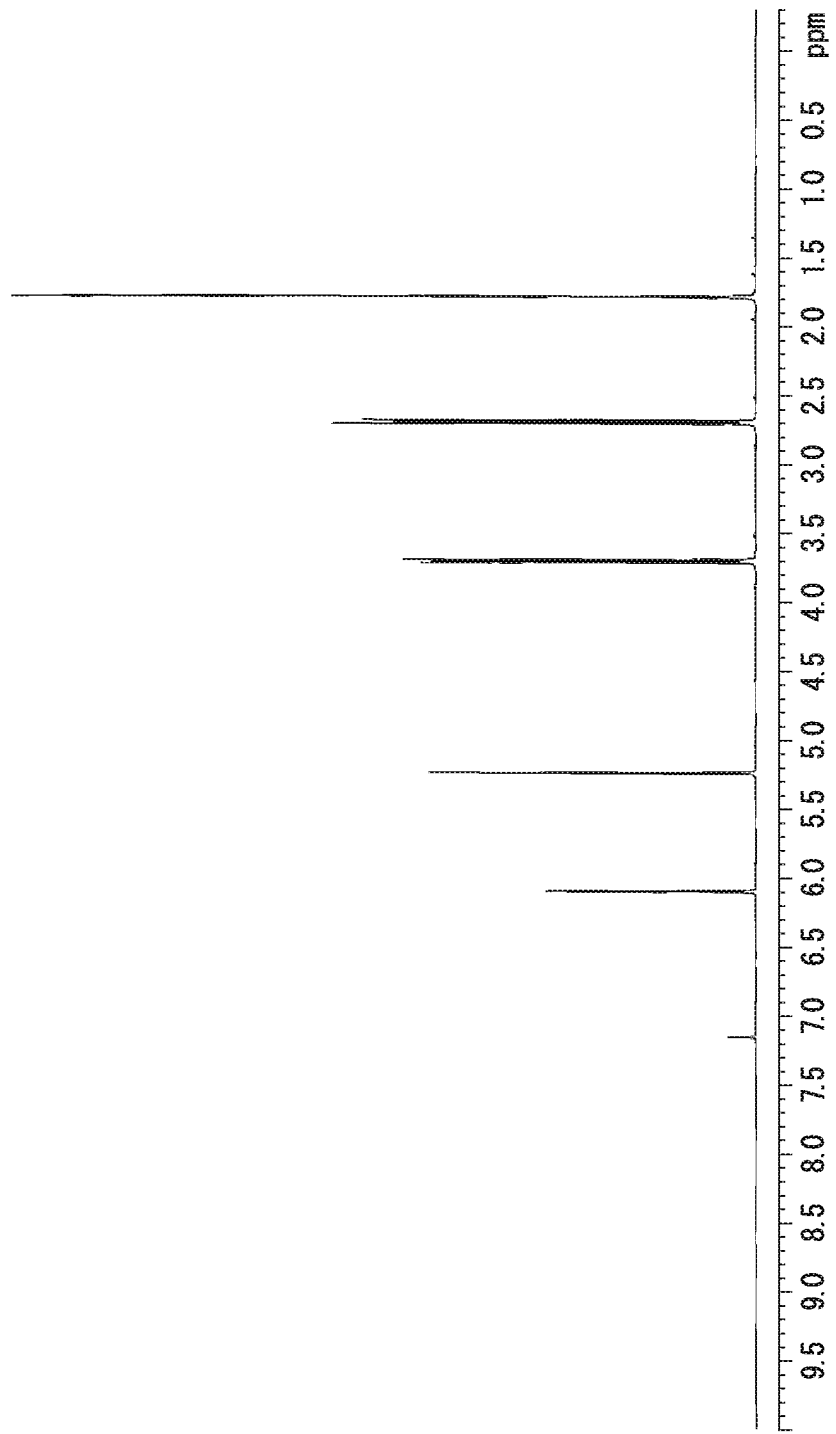
FIG. 5 is an NMR chart of a composition containing MOI as a polymerizable compound (A) and MOC as a reaction accelerator (B).
Figure 6:
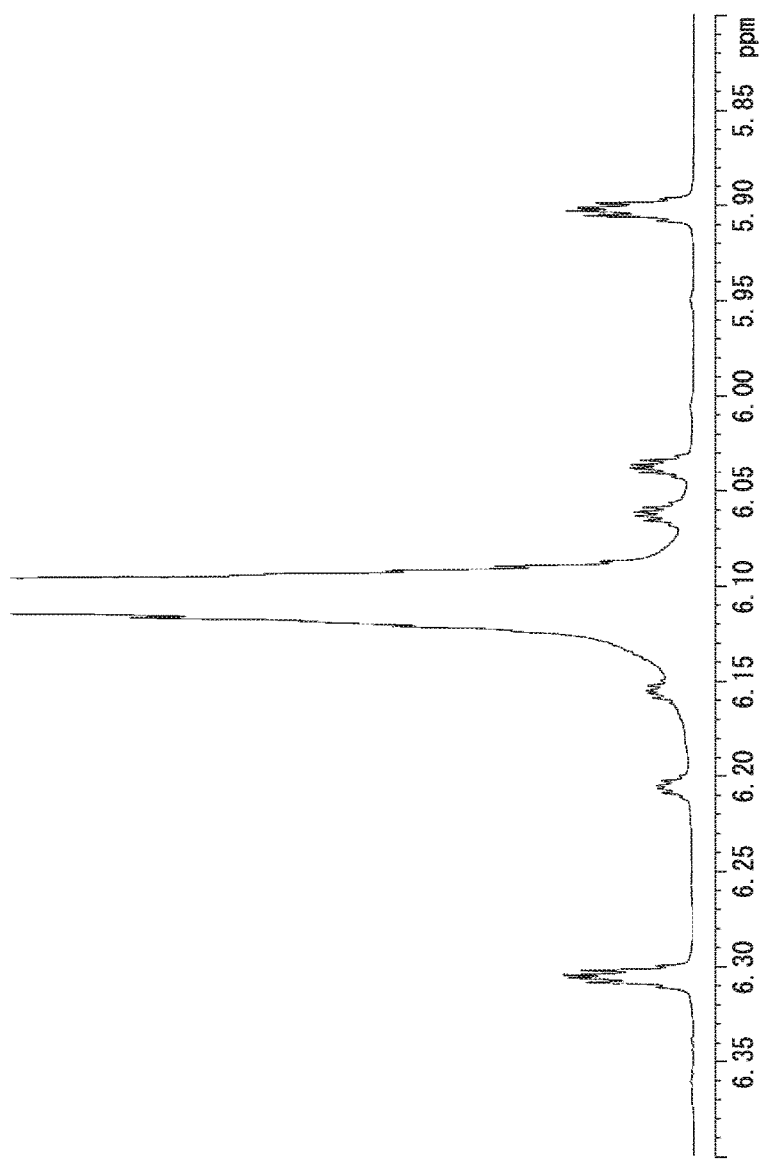
FIG. 6 is a partially enlarged view showing a range of around 5.85 to 6.35 of δ (ppm) of the NMR chart shown in FIG. 5.

NMR charts of the mixture are shown in FIGS. 5 and 6 (wherein the charts are spectra of a composition containing MOI and MOC and the content ratio of MOC to MOI is 3330 ppm by mass). FIG. 5 is an NMR chart (horizontal axis: δ (chemical shift) and vertical axis: signal intensity) showing a range of around 0.5-9.5 of δ (ppm) obtained by performing NMR measurement using tetramethylsilane (TMS) as an internal reference substance. FIG. 6 is an enlarged view showing a range of around 5.85 to 6.35 of δ (ppm) of the NMR chart shown in FIG. 5.

In the present chart, a peak detected in a range of around of 2.2 to 4.3 of δ (ppm) is a peak corresponding to four protons of an ethylene group included in both of MOI and MOC. Meanwhile, the integration value of a peak in a range of 6.02 to 6.05 of δ (ppm) corresponds to two protons on the terminal of a methacrylic group of MOC.

Samples are prepared by adding various amounts of the reaction accelerator (B) in a range of 100 ppm by mass to 3330 ppm by mass in the polymerizable compound (A) and uniformly dissolving 100 mg of the samples in 0.3 mL of dehydrated benzene d6, and respective $^1$H-NMR spectra are measured under the above-described conditions. A calibration curve of an intensity ratio regarding the two peaks with respect to the amount of MOC to be added is created based on the aforementioned measured values.

The amount of MOC contained in a composition is acquired by measuring NMR of the composition to be measured under the same conditions as those described above and plotting the above-described calibration curve.

(Combination of Polymerizable Compound (A) and Reaction Accelerator (B))

Each of the polymerizable compound (A) and the reaction accelerator (B) contained in the composition (I) may be used alone or a combination of two or more kinds thereof may be used.

In the present invention, it is preferable that a structure in which an isocyanate group is removed from at least one kind of polymerizable compound (A) contained in the composition (I) is the same as a structure in which a halogenated carbamoyl group is removed from at least one kind of reaction accelerator (B) contained in the composition (I).

For example, in a case where the polymerizable compound (A) includes a compound represented by the formula (1), it is preferable that the reaction accelerator (B) contains a compound which is represented by the formula (2) and in which $R^1$, $R^2$, and $R^3$ in the formula (2) are respectively the same as $R^1$, $R^2$, and $R^3$ included in the polymerizable compound (A). In a case where the polymerizable compound (A) contains a compound represented by the formula (1'), it is preferable that the reaction accelerator (B) contain a compound which is represented by the formula (2') and in which $R^1$, $R^2$, and $R^3$ in the formula (2') are respectively the same as $R^1$, $R^2$, and $R^3$ included in the polymerizable compound (A).

As described above, when the structure in which an isocyanate group is removed from the polymerizable compound (A) is the same as the structure in which a halogenated carbamoyl group is removed from the reaction accelerator (B), the yield of a target reaction product is improved in a reaction of, for example, the polymerizable compound (A) with a compound having an active hydrogen-containing group described below.

(Optional Components)

The composition (I) may be a composition which consists of the polymerizable compound (A) and the reaction accelerator (B) or a composition which further contains other component (optional component) other than the polymerizable compound (A) and the reaction accelerator (B).

As the optional component, for example, compounds, other than the polymerizable compound (A) and the reaction accelerator (B), which can be reacted with the polymerizable compound (A) (other reactive compounds) can be cited.

In a case where a (meth)acryloyl group of the polymerizable compound (A) is reacted, a polymerizable compound (another polymerizable compound) including a polymerizable functional group such as an ethylenically unsaturated group is preferably used as the above-described other reactive compound. Other reactive compounds are not particularly limited and can be suitably selected from various radically polymerizable monomers according to the purpose thereof.

In a case where an isocyanate group of the polymerizable compound (A) is reacted, a compound having an active hydrogen-containing group (hereinafter, also referred to as an active hydrogen-containing compound) is preferably used as the above-described other reactive compound.

In the present invention, it is particularly preferable that the composition (I) contains an active hydrogen-containing compound. This is because the reaction accelerator (B) shows excellent reaction acceleration effects particularly during the reaction of an isocyanate group of the polymerizable compound (A) with the active hydrogen-containing group (particularly a hydroxyl group).

(Active Hydrogen-Containing Compound)

The active hydrogen-containing compound includes an active hydrogen-containing group.

The active hydrogen is a hydrogen atom bonded to a nitrogen atom, an oxygen atom, a sulfur atom or the like, and has higher reactivity than that of a hydrogen atom bonded to a carbon atom.

The active hydrogen-containing group is not particularly limited as long as the structure thereof has active hydrogen. At least one selected from a group consisting of a hydroxyl group, a mercapto group, a carboxyl group, and an amino group is preferable as the active hydrogen-containing group, and a hydroxyl group is particularly preferable in terms of reactivity.

Examples of the compound having a hydroxyl group as an active hydrogen-containing group include monoalcohols such as $R^4OH$ ($R^4$ represents an alkyl group having 1 to 10 carbon atoms); hydroxyalkyl(meth)acrylate such as 2-hydroxyethyl(meth)acrylate, hydroxypropyl(meth)acrylate, 2,3-dihydroxybutyl(meth)acrylate. 4-hydroxybutyl(meth) acrylate, 6-hydroxyhexyl(meth)acrylate, or 8-hydroxyoctyl (meth)acrylate; vinyl ethers such as 2-hydroxyethyl vinyl ether and 4-hydroxybutyl vinyl ether; a monoesterified product of polyhydric alcohol and (meth)acrylic acid such as 4-hydroxymethyl cyclohexyl(meth)acrylate or polyalkylene glycol mono(meth)acrylate; a hydroxyl group-containing compound obtained by performing ring-opening polymerization of ethylene oxide or propylene oxide or a compound obtained by performing ring-opening polymerization of ε-caprolactone wherein the above-described monoesterified product of a polyhydric alcohol and (meth)acrylic acid is used; polyhydric alcohol such as ethylene glycol, diethylene glycol, triethylene glycol, propylene glycol, dipropylene glycol, 1,3-butylene glycol, 1,4-butylene glycol, glycerin, diglycerin, D-glucose, D-glucitol, isopropylene glycol, butanediol, 1,5-pentanediol, 1,6-hexanediol. 1,9-nonanediol, or neopentyl glycol; polyalkylene glycols such as polyethylene glycol, polypropylene glycol, polybutylene glycol, and polytetramethylene glycol, and polymer polyols such as polycaprolactonediol, polycaprolactone triol, and polycarbonate diol.

Examples of the compound having a mercapto group as an active hydrogen-containing group include monothiol such as 1-butanethiol, 1-pentane thiol, 1-octanethiol, 1-dodecanethiol, n-octanedecanethiol, α-toluenethiol, 2-benzimidazole thiol, 2-thiazoline-2-thiol, 2-methyl-2-propanethiol, or O-aminothiophene; and polyvalent thiol such as hexane dithiol, decane dithiol, 1,4-butanediol bisthiopropionate, 1,4-butanediol bisthioglycolate, ethylene glycol bisthioglycolate, ethylene glycol bisthiopropionate, trimethylol propane tristhioglycolate, trimethylol propane tristhiopropionate, trimethylol propane tris(3-mercaptobutyrate), pentaerythritol tetrakis thioglycolate, pentaerythritol tetrakis thiopropionate, trimercaptopropionic acid tris(2-hydroxyethyl) isocyanurate, 1,4-dimethylmercaptobenzene, 2,4,6-trimercapto-s-triazine, 2-(N,N-dibutylamino)-4,6-dimercapto-s-triazine, tetraethylene glycol bis 3-mercaptopropionate, trimethylol propane tris 3-mercaptopropionate, tris(3-mercaptopropinyloxyethyl) isocyanurate, pentaerythritol tetrakis 3-mercaptopropionate, dipentaerythritol tetrakis 3-mercaptopropionate, 1,4-bis(3-mercaptobutyloxy) butane, 1,3,5-tris(3-mercaptobuytloxyethyl)-1,3,5-triazine-2,4,6(1H,3H,5H)-trione, or pentaerythritol tetrakis (3-mercaptobutyrate).

Examples of the compound having a carboxyl group as an active hydrogen-containing group include monocarboxylic acid such as acetic acid or propionic acid: aliphatic-aromatic polycarboxylic acid such as succinic acid, adipic acid, dimer acid, phthalic acid, isophthalic acid, terephthalic acid, trimellitic acid, or pyromellitic acid; and polymer polycarboxylic acid such as a (co)polymer of polyamic acid and acrylic acid.

Examples of the compound having an amino group as an active hydrogen-containing group include monoamine such as butylamine, hexylamine, or aniline; aliphatic polyamine such as diethylene triamine, triethylene tetramine, 1.3- or 1,4-bisaminomethylcyclohexane, isophorone diamine, hexamethylene diamine, or bis(4-aminocyclohexyl) methane; aromatic polyamine such as m- or p-xylylene diamine, bis(4-aminophenyl) methane, or 2,4- or 2,6-trylene diamine; glycosamines such as chitosane; and a silicone compound such as bis(3-aminopropyl)polydimethyl siloxane, or bis(3-aminopropyl)polydiphenyl siloxane.

In regard to the amount of the active hydrogen-containing compound in the composition (I), the molar ratio of the isocyanate group included in the polymerizable compound (A) to the active hydrogen-containing group of the active hydrogen-containing compound is preferably in a range of 1:3 to 3:1 (isocyanate group: active hydrogen-containing group) and is more preferably in a range of 1.2:1 to 1:1.2.

A polymerization inhibitor is an exemplary example of an optional component other than other reactive compounds. As the polymerization initiator, a phenolic compound or a hydroquinone-based compound which are generally used to prevent polymerization can be used, and specific examples thereof include hydroquinone, methoxyhydroquinone, catechol, p-tert-butylcatechol, cresol, dibutyl hydroxy toluene (BHT), and 2,4,6-tri-tert-butylphenyl.

For the purpose of dilution, an inactive solvent may be contained as an optional component because it is easily handled. An inactive solvent is a solvent which does not contain active hydrogen and examples thereof include toluene, xylene, hexane, ethyl acetate, tetrahydrofuran, n-butyl acetate, cyclohexanone, and methyl isobutyl ketone.

In addition, a curing catalyst (a thermal curing catalyst or a photo-curing catalyst), a photo-radical initiator, a curing agent, a curing accelerator, an additive (a filler, a defoaming agent, a flame retardant, an antioxidant, an ultraviolet absorber, a stress reducing agent, a flexibility imparting agent, waxes, a resin, a crosslinking agent, a halogen trapping agent, a leveling agent, or a wetting properties-improving agent) may be included as needed.

Examples of the curing catalyst include a thermal acid generator and a photoacid generator. As the thermal acid generator or the photoacid generator, diazonium salts, iodonium salts, sulfonium salts, phosphonium salts, selenium salts, oxonium salts, or ammonium salts can be used. The curing catalyst may be used alone or a combination of two or more kinds thereof may be used.

The amount of the curing catalyst to be added is in a range of 0.05 parts by mass to 10 parts by mass and preferably in a range of 0.5 parts by mass to 5 parts by mass with respect to 100 parts by mass of the total amount of the composition.

Examples of the photo-radical initiator include benzophenone, benzyl acetophenone, benzyl dimethyl ketone, benzoin, benzoin methyl ether, benzoin ethyl ether, benzoin isopropyl ether, dimethoxy acetophenone, dimethoxy phenyl acetophenone, diethoxy acetophenone, diphenyl disulfite, methyl ortho-benzoyl benzoate, ethyl 4-dimethylaminobenzoate, 2,4-diethyl thioxanthone, 2-methyl-1-(4-methylthiophenyl)-2-morpholinopropan-1-one, 3,3',4,4'-tetra(t-butylperoxycarbonyl)benzophenone, 2-hydroxy-2-methyl-1-phenyl-propane-1-one, 4,4-bisdiethylaminobenzophenone, and 2,2'-bis(2- chlorophenyl)-4,5,4',5'-tetraphenyl-1,2'-biimidazole. These may be used alone or a combination of two or more kinds thereof may be used, and a photosensitizer may be added if necessary.

Examples of the curing agent include a phenolic resin and an acid anhydride.

As a phenolic resin, a resin in which phenol or cresol is polymerized using formaldehyde can be used. The resin may be a resin obtained by copolymerizing an alicyclic compound or an aromatic compound such as dicyclopentadiene, naphthalene, or biphenyl. The amount of the phenolic resin to be mixed is normally in a range of 0 part by mass to 200 parts by mass and can be suitably selected within a range of 5 parts by mass to 200 parts by mass with respect to 100 parts by mass of the total amount of the composition.

A polybasic acid anhydride is an exemplary example of an acid anhydride, and specific examples thereof include phthalic anhydride, trimellitic anhydride, pyromellitic anhydride, a benzophenone tetracarboxylic anhydride, 4-tetrahydrophthalic anhydride, 4-methyl-4-tetrahydrophthalic anhydride, 3-methyl-4-tetrahydrophthalic anhydride, nadic anhydride, methyl nadic anhydride, a hydrogenated methyl nadic anhydride. 4-(4-methyl-3-pentenyl)tetrahydrophthalic anhydride, succinic anhydride, adipic anhydride, maleic anhydride, sebacic anhydride, dodecanedioic anhydride, a methyl cyclohexene tetracarboxylic anhydride, dodecenyl succinic anhydride, hexahydrophthalic anhydride, 4-methylhexahydrophthalic anhydride, 3-methylhexahydrophthalic anhydride, a vinyl ether-maleic anhydride copolymer, and an alkyl styrene maleic anhydride copolymer. The amount of the acid anhydride to be mixed is normally in a range of 0 parts by mass to 160 parts by mass and can be suitably selected within a range of 20 parts by mass to 160 parts by mass with respect to 100 parts by mass of the total amount of the composition.

The curing accelerator is not particularly limited as long as the agent is normally used, and examples thereof include a diazabicycloundecene-based curing accelerator (diazabicycloalkenes); a phosphorus-based curing accelerator such as phosphoric acid ester or phosphines; and an amine-based curing accelerator such as a tertiary amine or quaternary ammonium salts. Examples of the diazabicycloundecene-based accelerator include 1,8-diazabicyclo[5,4,0]undecene-7 (DBU) and salts thereof (organic acid salts such as octylate, sulfonate, ortho-phthalate, or phenate).

Specific examples of other curing accelerators include known compounds, for example, a tertiary amine such as benzyldimethylamine, 2,4,6-tris(dimethylaminomethyl) phenol, trimethylamine, or triethylene diamine; imidazoles such as 2-ethyl-4-methyl imidazole, and 1-cyanoethyl-2-ethyl-4-methylimidazole; a phosphorus compound (phosphonium salts or the like) which does not contain an aromatic group such as tetra-n-butylphosphonium-O,O-diethylphosphorodithioate; tertiary amine salts: quaternary ammonium salts; an organic tin compound such as tin octylate, dibutyl tin diacetate, dibutyl tin dilaurate, dibutyl tin oxide, or dioctyl tin oxide; and metal salts, for example, an organic bismuth compound such as bismuth octylate or bismuth decanoate. Moreover, metal organic acid salts can be used together with organic acid salts of the above-described diazabicycloalkenes. Examples of the metal organic acid salts include tin octylate, tin naphthenate, zinc octylate, and zinc naphthenate.

The amount of the curing accelerator in the composition (I) can be suitably selected within a range of 0.00001 parts by mass to 5 parts by mass with respect to 100 parts by mass of the total amount of the composition.

Fine particles such as glass fine particles, metal oxide fine particles, rubber fine particles, or ceramic fine particles may be mixed with the composition (I). In addition, fibers such as glass fibers or Kepler fibers may be mixed with the composition (I). These may be used alone or a combination of two or more kinds thereof may be used.

(Method of Producing Composition (I))

As a method of producing the composition (I), a method (i) of adding a reaction accelerator (B) to the polymerizable compound (A) or a method (ii) of generating the reaction accelerator (B) as a by-product when the polymerizable compound (A) is produced such that the reaction accelerator (B) coexists in a reaction product is an exemplary example. According to such methods, it is possible to produce a mixture of the polymerizable compound (A) and the reaction accelerator (B).

In a case where the composition (I) contains optional components, the composition (I) can be obtained by adding optional components to the mixture obtained in the above-described manner.

An operation of adjusting the solid content concentration thereof if necessary, exchanging a solvent, performing a filtration treatment, performing purification through precipitation or reprecipitation, or dissolving the composition in the solvent may be performed.

In the method (i), commercially available products may be respectively used for both of the polymerizable compound (A) and the reaction accelerator (B) or products produced by a known production method may be used.

Examples of the commercially available products of the polymerizable compound (A) include Karenz MOI (registered trademark, manufactured by Showa Denko K.K., methacryloyloxy ethyl isocyanate), Karenz AOI (registered trademark, manufactured by Showa Denko K.K, acryloyloxy ethyl isocyanate), Karenz MOI-EG (registered trademark, manufactured by Showa Denko K.K., methacryloyloxy ethoxy ethyl isocyanate), and Karenz BEI (registered trademark, manufactured by Showa Denko K.K., 1,1-(bisacryloyloxymethyl)ethyl isocyanate).

A method described in U.S. Pat. No. 2,821,544A is an exemplary example of the method of producing the polymerizable compound (A).

In a case of the method (ii), the reaction accelerator (B) can be produced by adding a halogenated compound to a reaction system during the process of producing the polymerizable compound (A) and changing the isocyanate group in the polymerizable compound (A) into a halogenated carbamoyl group. Further, in the case of this method, a structure other than the isocyanate group of the polymerizable compound (A) is the same as a structure other than the halogenated carbamoyl group of the reaction accelerator (B).

In the method (ii), a known production method described above can be employed as the method of producing the polymerizable compound (A).

Examples of the halogen compound to be used to change the isocyanate group to the halogenated carbamoyl group include phosgene and hydrogen chloride.

In the method (i) or (ii), as a method of producing a mixture of the polymerizable compound (A) and the reaction accelerator (B) after the process of producing the reaction accelerator (B), the following methods 1) and 2) are exemplary examples.

1) A method of blowing hydrogen chloride gas to a compound having a (meth)acryloyl group and an isocyanate group, extracting a deposited solid (reaction accelerator (B))

to produce the reaction accelerator (B), and then mixing the reaction accelerator (B) with the polymerizable compound (A).

2) A method of generating the reaction accelerator (B) as a by-product using phosgene or hydrogen chloride during a process of synthesizing the polymerizable compound (A) to obtain a mixture of the polymerizable compound (A) and the reaction accelerator (B).

Method of Using Composition (I)

A method of using composition (I) is not particularly limited, but the composition (I) is preferably used for an application of utilizing two stages of reactions in which any one of a (meth)acryloyl group and an isocyanate group included in the polymerizable compound (A) is allowed to be reacted and then another group included in a reaction product in a state of remaining unreacted is allowed to be reacted.

For example, a (meth)acryloyl group of a reaction product can be reacted (radical polymerization or the like with other molecules or other polymerizable compounds in the same reaction product) after a reaction (reaction or the like with an active hydrogen-containing group included in an active hydrogen-containing compound) of an isocyanate group of the polymerizable compound. On the contrary, an isocyanate group of the reaction product can be reacted (reaction or the like with the active hydrogen-containing group included in the active hydrogen-containing compound) after a reaction (radical polymerization or the like with other molecules or other polymerizable compounds in the same reaction product) of a (meth)acryloyl group of the polymerizable compound (A).

In a case where the (meth)acryloyl group is reacted (polymerized) with a polymerizable functional group of another polymerizable compound at the second stage, another polymerizable compound may be contained in the composition (I) in advance before the first stage of reaction is started or may be added to a reaction system after the first stage of reaction is finished.

In a case where the isocyanate group is reacted with an active hydrogen-containing group at the second stage, the active hydrogen-containing compound may be contained in the composition (I) in advance before the first stage of reaction is started or may be added to a reaction system after the first stage of reaction is finished. It is preferable that the active hydrogen-containing compound is added to a reaction system after the first stage of reaction is finished.

In the present invention, it is preferable that the composition (I) contains an active hydrogen-containing compound and the composition (I) is used for an application that utilizes two stages of reactions in which the polymerizable compound (A) is reacted with the active hydrogen-containing compound and then the reaction product is radically polymerized.

A curable composition is obtained when the polymerizable compound (A) is reacted with the active hydrogen-containing compound, and the details will be described below. Such a curable composition can be cured by promoting radical polymerization through irradiation with light or ultraviolet (UV) rays and can be used for various applications. In the present invention, the reaction rate between the polymerizable compound (A) and the active hydrogen-containing compound increases, in contrast to a case where the reaction accelerator (B) is not present, by carrying out the reaction of the polymerizable compound (A) with the active hydrogen-containing compound in the presence of the reaction accelerator (B) and the reaction can be completed in a short period of time. Therefore, the productivity of a curable composition is improved.

Curable Composition and Cured Product

In a case where the composition (I) contains an active hydrogen-containing compound, a curable composition having curing properties is obtained by carrying out a reaction of the polymerizable compound (A) with the active hydrogen-containing compound in the composition (I).

The reaction product generated through the above-described reaction is a polymerizable compound which has a structure in which the polymerizable compound (A) is connected to the active hydrogen-containing compound through a bond formed by the reaction of an isocyanate group with an active hydrogen-containing group and includes a (meth)acryloyl group derived from the polymerizable compound (A).

In the reaction of an isocyanate group with an active hydrogen-containing group, a urethane bond (—NH—CO—O—) is formed when the active hydrogen-containing group is a hydroxyl group, a thiourethane bond (—NH—CO—S—) is formed when the active hydrogen-containing group is a mercapto group, an amide bond (—NH—CO—) is formed when the active hydrogen-containing group is a carboxyl group, and a urea bond (—NH—CO—NH—) is formed when the active hydrogen-containing group is an amino group.

Consequently, in a case where the active hydrogen-containing compound includes at least one selected from a group consisting of a hydroxyl group, a mercapto group, a carboxyl group, and an amino group as active hydrogen-containing groups, the curable composition obtained by the above-described reaction contains a polymerizable compound including a (meth)acryloyl group and at least one selected from a group consisting of a urethane bond, a thiourethane bond, an amide bond, and a urea bond in a molecule.

The process of reacting the polymerizable compound (A) with the active hydrogen-containing compound can be performed according to a method of adding the active hydrogen-containing compound to a composition that contains the polymerizable compound (A) and the reaction accelerator (B) at a predetermined reaction temperature or a method of adding the polymerizable compound (A) to the composition that contains the active hydrogen-containing compound and the reaction accelerator (B) at a predetermined reaction temperature.

The reaction temperature is preferably in the range of 40° C. to 80° C. and is more preferably in the range of 50° C. to 70° C. When the reaction temperature is 80° C. or higher, there is a possibility that the reactivity of a double bond in the polymerizable compound (A) is increased so that a polymerization reaction is promoted, which is not preferable. Meanwhile, when the reaction temperature is 40° C. or lower, the reaction speed is reduced, which is not preferable.

The reaction time is not particularly limited and can be suitably set according to the state in which the reaction is promoted.

After the reaction, an additive may be added to the curable composition if necessary.

When a treatment of irradiating the curable composition obtained in the above-described manner with light or ultraviolet (UV) rays is further performed, radical polymerization of a polymerizable compound including a polymerizable functional group such as a (meth)acryloyl group is promoted in the curable composition, thereby obtaining a cured product.

Such a curable composition can be used for coating materials, inks, additives, coating agents, electronic materials (liquid resists, film resists, color filter resists, tapes for a semiconductor, gluing agents, and adhesives), printing (press plates and color calibration), medical care (soft contact lenses and dental materials), fibers, paper, and wood (surface treatment agents), automobiles (top coats, coating materials for repair, and coating materials for a component), consumer electrical appliances (substrates and insulating materials), and building materials (cement primer, coating materials, and adhesives).

EXAMPLES

Hereinafter, the present invention will be described in detail with reference to examples, but the present invention is not limited to these examples.

In respective examples described below, "%" indicates "% by mass" (wt %) and "ppm" indicates "ppm by mass" (wt ppm) unless otherwise noted.

The conditions of liquid chromatography analysis (hereinafter, referred to as "LC analysis") are as follows.

Column: trade name: "Shodex (registered trademark) KF-801" manufactured by Showa Denko K.K., four columns
Eluent: tetrahydrofuran (THF)
Flow rate: 0.8 mL/min
Oven temperature: 40° C.
Detector: differential refractive index (RI), UV (wavelength of 210 nm)
(Method of Preparing Reaction Accelerator (B))

Synthesis Example 1

10.0 g of methacryloyloxy ethyl isocyanate (Karenz MOI (registered trademark), Showa Denko K.K., hereinafter, referred to as "MOI") was added to a 100 mL three-neck flask and 2.58 g of dry hydrogen chloride was bubbled to the methacryloyloxy ethyl isocyanate through an inner intubation while the inner temperature of the flask was decreased to 15° C., thereby obtaining 12.6 g of methacryloyloxy ethyl carbamoyl chloride (hereinafter, referred to as "MOC"). The purity was 100%.

Synthesis Example 2

110 g of aminoethyl methacrylate hydrochloride (hereinafter, referred to as "AEMHCl") was added to 200 g of toluene, 110 g of phosgene was supplied thereto in a state in which AEMHCl was melted at an inner temperature of 85° C., and MOI was synthesized. The dissolved phosgene was removed by bubbling nitrogen to a reaction solution and toluene serving as a solvent was distilled under reduced pressure, thereby obtaining 110 g of crude MOI.

When the amount of MOC in the crude MOI was confirmed using silver nitrate titration, the value was 10.8%.
(Effects of Accelerating Urethanization Reaction Due to Addition of Reaction Accelerator (B))

Example 1

6.21 g of MOI, 0.0186 g (corresponding to 3000 ppm with respect to MOI) of methacryloyloxy ethyl carbamoyl chloride (hereinafter, referred to as "MOC") produced in Synthesis Example 1, 50 mL of toluene, and 0.1 g of BHT were added to a 100 mL three-neck flask and the mixture was stirred and mixed. The obtained mixture was heated to 60° C., 8.89 g of n-butanol was further added to a system, and a reaction of MOI with n-butanol (urethanization reaction) was carried out. During the reaction, the temperature of the reaction solution was maintained at 60° C.

The time point when n-butanol was added was set as 0 time in the reaction described above, the reaction solution was sampled at respective time points when elapsed times (reaction times) from 0 time were 0 minute, 10 minutes, 30 minutes, 60 minutes, and 120 minutes, LC analysis was performed, and the rate (conversion rate) of MOI, in which an isocyanate group was converted into urethane, from used MOI was acquired based on the following formula. The amount (%) of MOI in the reaction solution was measured by LC analysis. The results are listed in Table 1 and shown in FIG. 1.

Conversion rate (%)=(amount (%) of MOI in prepared solution[before reaction]−amount (%) of MOI in reaction solution at sampling time)/(amount (%) of MOI in prepared solution[before reaction])×100

Example 2

The urethanization reaction was performed and the conversion rate was measured in the same manner as in Example 1 except that the amount of MOC to be added was changed to 0.0932 g (corresponding to 15000 ppm with respect to MOI). The results are listed in Table 1 and shown in FIG. 1.

Example 3

The urethanization reaction was performed and the conversion rate was measured in the same manner as in Example 1 except that the amount of MOC to be added was changed to 0.03 g (corresponding to 5 wt ppm with respect to MOI). The results are listed in Table 1 and shown in FIG. 1.

Comparative Example 1

The urethanization reaction was performed and the conversion rate was measured in the same manner as in Example 1 except that MOC was not added. The results are listed in Table 1 and shown in FIG. 1.

Example 4

Figure 2:
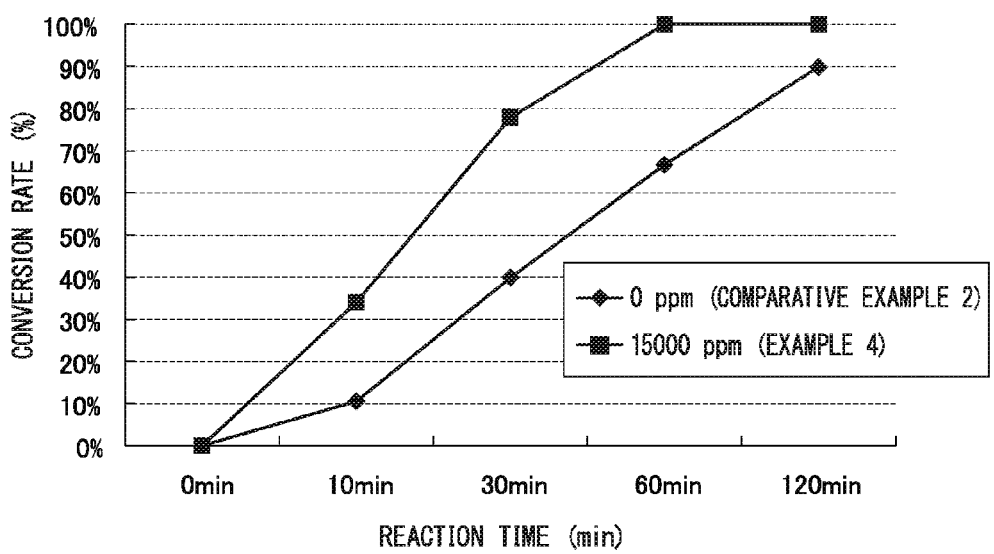
FIG. 2 is a graph showing results of Example 4 and Comparative Example 2 in which a urethanization reaction of AOI is performed (change in the conversion ratio of an isocyanate group of AOI to urethane with time (urethanization rate)).

The urethanization reaction was performed and the conversion rate (rate of AOI, in which an isocyanate group was converted into urethane, from used AOI) was measured in the same manner as in Example 1 except that MOC was changed to 5.64 g of acryloyloxy ethyl isocyanate (Karenz AOI (registered trademark), manufactured by Showa Denko K.K., hereinafter, referred to as "AOI") and the amount of MOC to be added was changed to 0.0846 g (corresponding to 15000 ppm with respect to AOI). The results are listed in Table 1 and shown in FIG. 2.

Comparative Example 2

The urethanization reaction was performed and the conversion rate was measured in the same manner as in Example 4 except that MOC was not added. The results are listed in Table 1 and shown in FIG. 2.

TABLE 1

| | Polymerizable compound (A) | Amount of MOC (ppm) | Conversion rate | | | | |
|---|---|---|---|---|---|---|---|
| | | | 0 min | 10 min | 30 min | 60 min | 120 min |
| Comparative Example 1 | MOI | 0 | 0.0% | 17.6% | 41.5% | 64.4% | 85.4% |
| Example 1 | | 3000 | 0.0% | 21.5% | 52.5% | 78.9% | 97.4% |
| Example 2 | | 15000 | 0.0% | 45.9% | 94.6% | 100.0% | 100.0% |
| Example 3 | | 5 | 0.0% | 18.1% | 42.3% | 66.6% | 88.2% |
| Comparative Example 2 | AOI | 0 | 0.0% | 10.5% | 39.9% | 66.7% | 89.9% |
| Example 4 | | 15000 | 0.0% | 34.0% | 77.9% | 100.0% | 100.0% |

From the above-described results, it was confirmed that MOC functioned as a reaction accelerator in the reaction of isocyanate with alcohol (urethanization reaction).

(Effects of Accelerating Amidation Reaction Due to Addition of Reaction Accelerator (B))

Example 5

0.0932 g (corresponding to 15000 ppm with respect to MOI described below) of MOC produced in Synthesis Example 1, 6.89 g of decanoic acid, 64.52 g of propylene glycol monomethyl ether acetate (PGMAc), and 0.1 g of BHT were added to a 100 mL three-neck flask and the mixture was stirred and mixed. The obtained mixture was heated to 60° C., 6.21 g of MOI (Karenz MOI (registered trademark), manufactured by Showa Denko K.K.) was further added to a system, and a reaction of MOI with decanoic acid (amidation reaction) was carried out. During the reaction, the temperature of the reaction solution was maintained at 60° C.

Figure 3:
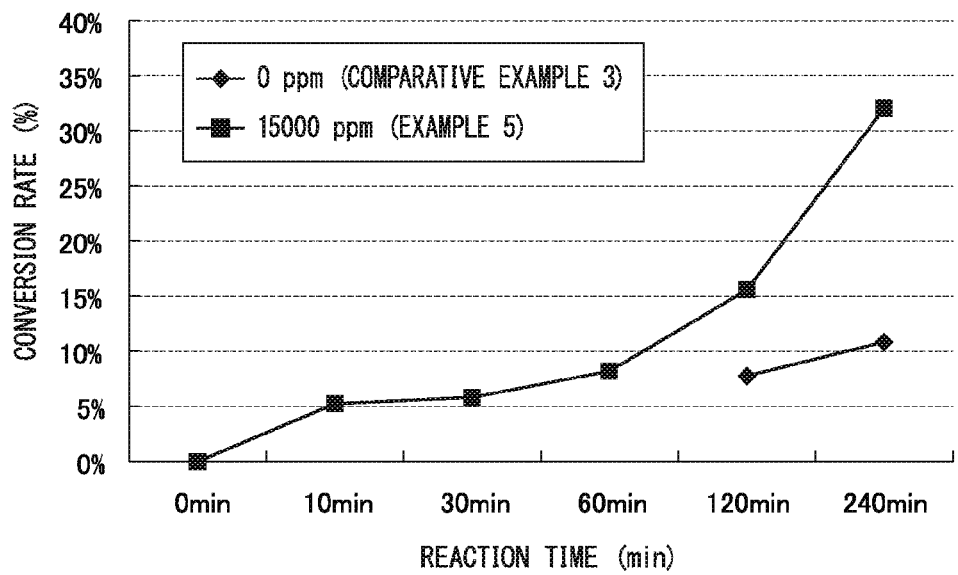
FIG. 3 is a graph showing results of Example 5 and Comparative Example 3 in which an amidation reaction of MOI is performed (change in the conversion ratio of an isocyanate group of MOI to amide with time (amidation rate)).

The time point when MOI was added was set as 0 time in the reaction described above, the reaction solution was sampled at respective time points when elapsed times (reaction times) from 0 time were 0 minute, 10 minutes, 30 minutes, 60 minutes, 120 minutes, and 240 minutes, LC analysis was performed, and the conversion rate thereof (rate of MOI, in which an isocyanate group was converted into amide, from used MOI) was measured. The conversion rate was acquired using the same formula as in Example 1. The results are listed in Table 2 and shown in FIG. 3.

Comparative Example 3

The amidation reaction was performed and the conversion rate was measured in the same manner as in Example 5 except that MOC was not added. The results are listed in Table 2 and shown in FIG. 3.

TABLE 2

| | Amount of MOC | 0 min | 10 min | 30 min | 60 min | 120 min | 240 min |
|---|---|---|---|---|---|---|---|
| Comparative Example 3 | 0 ppm | 0.0% | | | | 7.8% | 10.9% |
| Example 5 | 15000 ppm | 0.0% | 5.3% | 5.8% | 8.2% | 15.6% | 32.0% |

From the above-described results, it was confirmed that MOC functioned as a reaction accelerator in the reaction of isocyanate with carboxylic acid (amidation reaction).

(Comparison of Effects of Accelerating Urethanization Reaction Depending on Kinds of Reaction Accelerators to be Added)

Comparative Example 4

Figure 4:
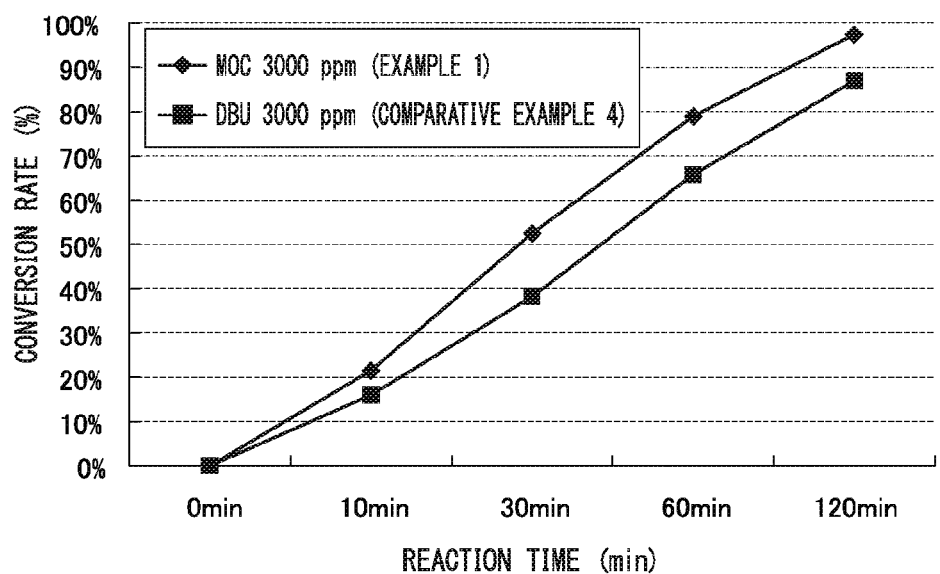
FIG. 4 is a graph showing results of Example 1 and Comparative Example 4 in which a urethanization reaction of MOI is performed (change in the conversion ratio of an isocyanate group of MOI to urethane with time (urethanization rate)).

The urethanization reaction was performed and the conversion rate was measured in the same manner as in Example 1 except that 0.02 g (corresponding to 3000 ppm with respect to MOI) of 1,8-diazabicyclo(5,4,0)undecene (hereinafter, referred to as "DBU," manufactured by Tokyo Chemical Industry Co., Ltd.) in place of MOC. The results are listed in Table 3 and shown in FIG. 4 together with the results of Example 1.

TABLE 3

| | Reaction accelerator | 0 min | 10 min | 30 min | 60 min | 120 min |
|---|---|---|---|---|---|---|
| Example 1 | MOC 3000 ppm | 0.0% | 21.5% | 52.5% | 78.9% | 97.4% |
| Comparative Example 4 | DBU 3000 ppm | 0.0% | 16.0% | 38.2% | 65.8% | 86.9% |

From the above-described results, it was understood that the reaction accelerator (B) of the invention of the present application had excellent reaction acceleration effects in the urethanization reaction compared to an amine-based catalyst.

(Difference in yield between MOI+MOC system and AOI+MOC system)

Example 6

The urethanization reaction was performed in the same manner as in Example 2 except that the reaction was continuously carried out for 1 hour without performing sampling on the reaction solution in the middle of the reaction.

When the reaction solution was LC-analyzed after the reaction, the ratio of a urethane compound having a methacryloyloxy ethyl group to a urethane compound which was generated by the reaction was 100% by mass (ratio of urethane having an acryloyloxy ethyl group was 0%).

Example 7

The urethanization reaction was performed in the same manner as in Example 4 except that the reaction was continuously carried out for 1 hour without performing sampling on the reaction solution in the middle of the reaction.

When the reaction solution was LC-analyzed after the reaction, the ratio of the amount of a urethane compound having a acryloyloxy ethyl group to that of a urethane compound generated by the reaction was 98.8% by mass and 1.2% by mass of a urethane compound having a methacryloyloxy ethyl group was contained. It is considered that this is because MOC used as the reaction accelerator (B) was changed to MOI in the reaction solution and MOI was reacted with n-butanol.

(Effects of Accelerating Radical Polymerization Reaction of Ethylenically Unsaturated Group Due to Reaction Accelerator (B))

Reference Example I 5.00 g of MOI (Karenz MOI (registered trademark), manufactured by Showa Denko K.K.) was redistilled and a contained polymerization inhibitor (BHT) was removed. 0.500 g (corresponding to 10000 ppm with respect to MOI) of MOC was added to distilled MOI, a composition obtained by mixing MOC with MOI was purged with nitrogen, and the resultant was heated at 100° C. When the temperature was observed, it was recognized that the temperature was increased at a time point when 20 minutes have elapsed from the time point of addition of MOC, and therefore the start of the reaction of a methacryloyl group (radical polymerization reaction) was confirmed.

Reference Example II

The same operation as in Reference Example I was performed except that MOC was not added. When the temperature was observed, it was recognized that the temperature was increased at a time point when 264 minutes have elapsed, and therefore the start of the reaction of a methacryloyl group (radical polymerization reaction) was confirmed.

From the results of Reference Examples I and II, it is confirmed that MOC exhibits not only an effect of accelerating the reaction of an isocyanate group in the polymerizable compound (A) but also an effect of accelerating a radical reaction of a (meth)acryloyl group.

However, in Reference Example I, it was confirmed that the radical reaction was started at a time point when 20 minutes were elapsed, which was significantly shorter than that of Reference Example II in spite of the condition in which the heating was performed without adding a radical polymerization initiator (that is, the condition was used which was not a normal photocuring reaction which was carried out by adding a photopolymerization initiator and performing UV irradiation). The result may be considered as an unpreferable state depending on the purpose of the application or an experimental operation because of storage stability thereof and from the following viewpoints.

In the present invention, since the polymerization compound (A) includes two functional points of an isocyanate group and a (meth)acryloyl group, it is preferable to produce a cured product by performing two stages of reactions in which the isocyanate group is reacted through heat in advance (first stage) and then the (meth)acryloyl group was reacted through light (second stage). However, when the amount of the reaction accelerator (B) is large during the reaction, the second-stage reaction may be unexpectedly promoted during the first-stage reaction.

From the above-described background, the amount of the polymerization accelerator (B) used in a reaction of a bifunctional monomer such as the polymerizable compound (A) is preferably in a range of 5 ppm by mass to 8000 ppm by mass and is more preferably in a range of 5 ppm by mass to 2000 ppm by mass with respect to the amount of the bifunctional monomer.

The invention claimed is:

1. A composition comprising:
   a polymerizable compound (A) which includes a (meth)acryloyl group and an isocyanate group in a molecule thereof; and
   a reaction accelerator (B) which is a compound including a (meth)acryloyl group and a halogenated carbamoyl group in a molecule thereof,
   wherein the amount of the reaction accelerator (B) is in a range of 5 ppm by mass to 20000 ppm by mass with respect to the amount of the polymerizable compound (A).

2. The composition according to claim 1, wherein the amount of the reaction accelerator (B) is in a range of 5 ppm by mass to 8000 ppm by mass with respect to the amount of the polymerizable compound (A).

3. The composition according to claim 1, wherein the polymerizable compound (A) is a compound represented by the following general formula (1) or (1')

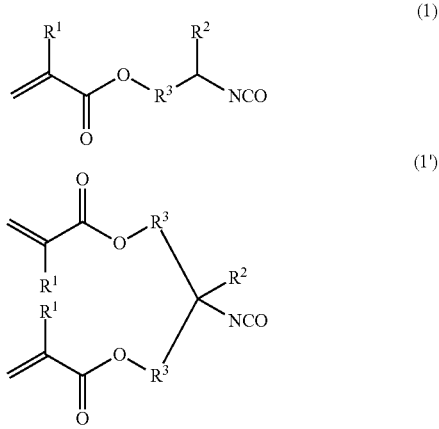

wherein, in the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from the group consisting of an ether bond, an ester bond, and a phenylene bond, and two $R^1$'s in the formula (1') may be the same as or different from each other and two $R^3$'s may be the same as or different from each other.

4. The composition according to claim 1, wherein the reaction accelerator (B) is a compound represented by the following general formula (2) or (2')

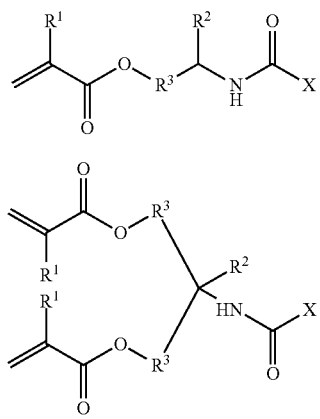

(2)

(2')

wherein, in the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from the group consisting of an ether bond, an ester bond, and a phenylene bond, X represents a fluorine atom, a chlorine atom, a bromine atom, or an iodine atom, and two $R^1$'s in the formula (2') may be the same as or different from each other and two $R^3$'s may be the same as or different from each other.

5. The composition according to claim 4,
wherein the polymerizable compound (A) contains a compound represented by the following formula (1) or (1')

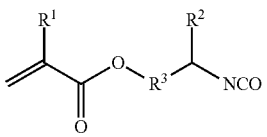

(1)

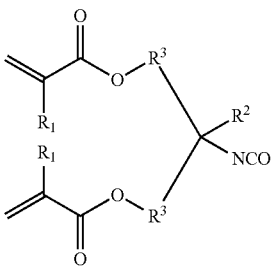

(1')

wherein, in the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from the group consisting of an ether bond, an ester bond, and a phenylene bond, and two $R^1$'s in the formula (1') may be the same as or different from each other and two $R^3$'s may be the same as or different from each other, and in the case where the polymerizable compound (A) contains a compound represented by the formula (1), the reaction accelerator (B) contains a compound which is represented by the formula (2) and in which R1, R2, and R3 in the formula (2) are respectively the same as R1, R2, and R3 included in the polymerizable compound (A), in the case where the polymerizable compound (A) contains a compound represented by the formula (1'), the reaction accelerator (B) contains a compound which is represented by the formula (2') and in which R1, R2, and R3 in the formula (2') are respectively the same as R1, R2, and R3 included in the polymerizable compound.

6. The composition according to claim 1, further comprising a compound which includes an active hydrogen-containing group.

7. The composition according to claim 6, wherein the active hydrogen-containing group is at least one selected from the group consisting of a hydroxyl group, a mercapto group, a carboxyl group, and an amino group.

* * * * *